United States Patent [19]

Nagaoka et al.

[11] Patent Number: 4,835,287
[45] Date of Patent: May 30, 1989

[54] ANTIBIOTIC SUBSTANCE

[75] Inventors: Katsuhiko Nagaoka, Tokyo; Masaru Matsumoto, Tomisato; Koichi Yokoi, Kashiwa; Junji Oono, Narita; Kenichi Kukita, Kashiwa; Toshiaki Nakashima, Shisui, all of Japan

[73] Assignee: SS Pharmaceutical Co., Ltd., Tokyo, Japan

[21] Appl. No.: 75,616

[22] Filed: Jul. 20, 1987

[51] Int. Cl.⁴ .................................. C07D 207/24
[52] U.S. Cl. .................................... 548/453
[58] Field of Search ......................... 548/453

[56] References Cited

FOREIGN PATENT DOCUMENTS 69992 3/1987 Japan .
149693 7/1987 Japan .

OTHER PUBLICATIONS

Chem. Pharm. Bull., vol. 34, (11), pp. 4554–4561, 1986, Yokoi et al: Azinomycins A and B, New Antitumor . .
. .
The Journal of Antibiotics, vol. 39 (11), 1986, pp. 1527–1532, Nagaoka et al: Azinomycins A and B, New Antitumor . . . .
The Journal of Antibiotics, vol. 40 (1), 1987, pp. 60–65, Ishizeki et al, Azinomycins A and B, New Antitumor .
. . .

Primary Examiner—David B. Springer
Attorney, Agent, or Firm—Oblon, Fisher, Spivak, McClelland & Maier

[57] ABSTRACT

A substance SS42227 represented by the following formula (I):

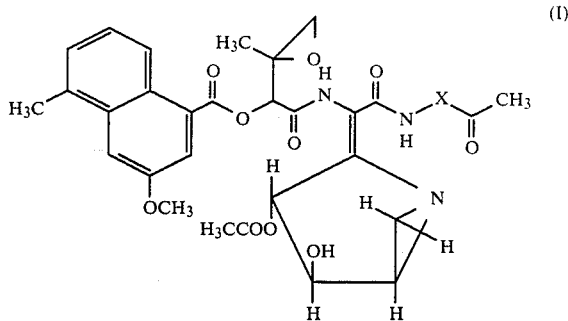

in which X represents $>CH_2$ or $>C=CHOH$. The substance has antimicrobial and antitumor activities, and thus is useful as a medicine.

3 Claims, 6 Drawing Sheets

ANTIBIOTIC SUBSTANCE

BACKGROUND OF THE INVENTION

1. Field of the Invention:

This invention relates to a substance SS42227 and the process for preparing the same.

2. Description of the Background:

Various substances which are known in the art are produced by microorganisms. Some of such substances are useful as a medicine, but there is still a strong need for a substance which possesses antimicrobial and antitumor activities and is thus effective for use as a medicine.

The present inventors have isolated a number of microorganisms from natural soils and conducted extensive studies on the product produced by such microorganisms. As a result, the inventors discovered that a strain separated from a soil at Itakura, Oora, Gunma Prefecture, Japan is capable of producing a novel substance having antimicrobial and antitumor activities. The discovery has led to the completion of this invention.

SUMMARY OF THE INVENTION

Accordingly, an object of this invention is to provide the substance SS42227 represented by the following general formula (I):

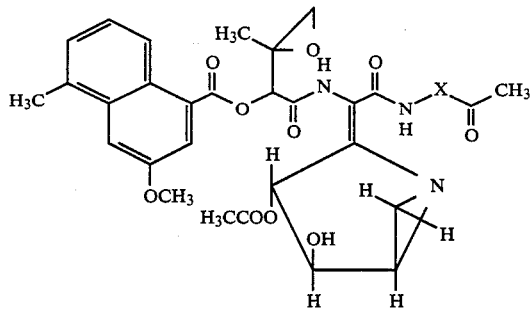
(I)

in which X represents >CH$_2$ or >C=CHOH, and a process for preparing the same.

DETAILED DESCRIPTION OF THE INVENTION AND PREFERRED EMBODIMENTS

Figure 1:
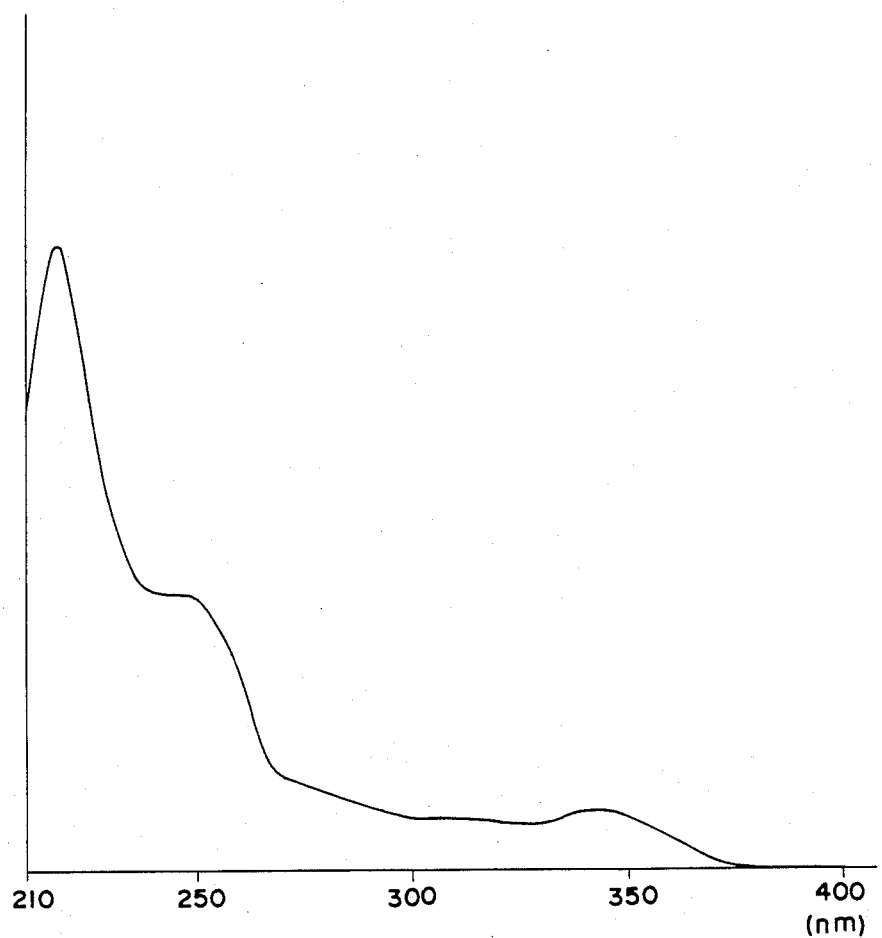
FIG. 1 shows the ultraviolet absorption spectrum of the substance SS42227A of this invention.

The substance SS42227 of this invention can be divided, depending on the kind of the substituent X, into SS42227 A represented by the following formula (Ia) and SS42227 B represented by the following formula (Ib):

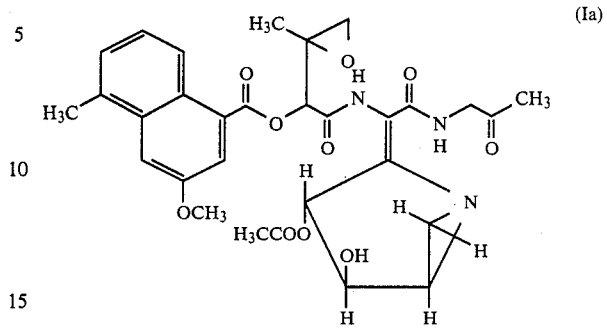
(Ia)

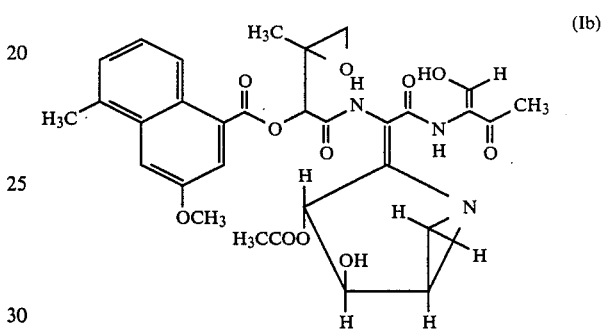
(Ib)

The strain S42227 which produces the substance SS42227 of this invention has the following characteristics:

(1) Morphology

Following characteristics were confirmed by the light and electron microscopes observations of the microorganisms of the S42227 strain cultured in various agar culture media at 28° C. for 10 to 14 days.

Sporogenesis hyphas are simply branched from an aerial mycelium. The branch has a spiral terminal. They are predominant in microorgainsms cultured in a sucrose-nitrate agar medium, oatmeal agar medium, calcium maleate agar medium and the like. No trochoid branch is observed. In the observations of conidia matured in an oatmeal agar culture medium, more than 10 chains of spores with each spore being of an oval of cylindrical shape of 0.7–0.9×1.0–1.3 μm are recognized. The surface of spores is smooth. No special structure such as a sporangia, flagellous spore and sclerotium is observed in the microoganisms cultured in various agar media. Fragmentation of substrate mycellium is not recognized.

(2) Growth characteristics on various culture media:

The growth characteristics of the S42227 strain on various culture media are shown in the Table in the next page. The observations were made on the microorganisms cultured at 28° C. for 14 days. In the table, designation of colors is based on the color series as defined by "Color Name Dictionary" (1981) published by Japan Color Research Institute Co. Figures in parentheses designate the color number.

| | | | Aerial mycelium | | Reverse | Soluble |
|---|---|---|---|---|---|---|
| | Medium | Growth | Formation | Color | Color | Pigment |
| 1. | Sucrose-nitrate agar | M | M | Lt. gy. br. (58) | Pale yellow (67) | None |
| 2. | Glucose-asparagine | M | M | White (202)- | Pale yellow (67) | None |

| | Medium | Growth | Aerial mycelium Formation | Aerial mycelium Color | Reverse Color | Soluble Pigment |
|---|---|---|---|---|---|---|
| | agar | | | lt. gy. br. (58) | | |
| 3. | Glycerol-asparagine agar (ISP medium 5) | M | M | White (202)–lt. gy. br. (58) | Pale yellow (67)–yellowish br. (50) | Pale brown |
| 4. | Glycerol-nitrate agar | M | P | White (202) | Pale yellow (67) | Pale brown |
| 5. | Starch agar (ISP medium 4) | M | M | White (202)–lt. gy. br. (58) | Pale yellow (67)–yellowish br. (50) | Pale yellow |
| 6. | Yeast extract-malt extract agar (ISP medium 2) | A | A | white (202)–gy. br. (60) | Yellowish br. (50) | None |
| 7. | Oatmeal agar (ISP medium 3) | A | A | Lt. gy. br. (58) | Pale yellow (67) | Pale yellow |
| 8. | Tyrosine agar (ISP medium 7) | M | M | White (202)–lt. gy. br. (58) | Yellowish br. (50) | Pale brown |
| 9. | Nutrient agar | M | Non | — | Lt. yellowish br. (48) | None |
| 10. | Calcium-malate agar | P | P | White (202)–lt. brownish gray (207) | Colorless | None |

Abbreviation: Lt.: light, gy.: grayish, br.: brown, M: Moderate, A: Abundant, P: Poor, (3) Physiological Characteristics a. Temperature range of growth, when cultured in yeast-malt agar culture medium for 14 days:
Optimum growth temperature: 24°–29° C.
Possible growth temperature: 11°–41° C.

b. Gelatin Liquefaction: positive c. Starch hydrolysis: positive d. Skimmed milk coagulation: negative Skimmed milk peptonization: positive e. Melanin-like pigment production: negative f. Nitrate reduction: positive g. Cellulose decomposition: negative (4) Carbon sources assimilation observed in the microorganism cultured in Pridham-Gottlieb agar culture medium:
Utilize L-arabinose, D-xylose, D-glucose, D-fructose, D-mannitol, D-gatactose and salicin, and do not utilize inositol, L-rhamnose, cellulose, sucrose, and raffinose.

(5) Diaminopimeric acid content:
LL-diaminopimeric acid was detected by the analysis of diaminopimeric acid in the total microorganism.

The above mycological characteristics of the strain of S42227 may be summarized as follows:

The aerial mycelium has spiral terminals and its conidia is in the form of a chain of more than 10 spores, with each spore having a smooth surface. The aerial mycelium is of gray-color series, the reverse side being of yellowish brown, and its soluble pigment is of faint brown. The aerial mycellium does not yield melanin-like pigment.

Based on these mycological characteristics of the S42227 strain and also based on the fact that it contains LL-diaminopimeric acid, S42227 was determined as a strain belonging to Streptomyces. Further, as there has been found no other strain of microorganism possessing the same mycological properties, the strain was named Streptomyces sp. S42227 and deposited to Fermentation Research Institute, Agency of Industrial Science and Technology, as FERM p-8443.

The substance SS42227 of this invention may be prepared by seeding the about strain of micoorganism in a culture medium containing nutrients and culturing it in an areobic conditions. Any strains of microorganisms may be employed for producing the substance SS42227 of this invention, inclusive of the above-mentioned S42227 strain and its artificial or natural variants, so long as the same is capable of producing the substance SS42227. The artificial variants of the strain S42227 may be easily obtained in the similar manner as those of other actinomycetes, for instance, by irradiation of ultraviolet rays or cobalt 60, or by the application of chemical mutagens.

Culturing of the microorganisms producing the substance SS42227 may be carried out in the following manner.

The microorganisms belonging to the strain of Streptomyces producing the substance SS42227 may be cultured according to the same procedures as applied for culturing common actinomycetes. Either of synthetic, semi-synthetic or natural culture media may be employed as a nutrient medium, so long as they appropriately contain assimilative cabon sources, nitrogen sources, inorganic materials and the like. Glucose, fructose, mannitol, starch, molasses, etc. may be used solely or in combination with others as carbon sources. Hydrocarbons, alcohols and organic acids may also be used depending on the assimilative ability of the bacteria. As nitrogen sources, inorganic or organic nitrogen compounds may be used. These nitrogen compounds include, for example, ammonium chloride, ammonium sulfate, ammonium nitrate, urea, sodium nitrate, sodium glutamate, as well as naturally available materials such as soybean flour, yeast extract, peptone, meat extract, dried yeast, cotton seed meal, proteose peptone, casamino acid, corn steep liquor and the likes. They may be used either solely or in combination with others. As inorganic materials, calcium carbonate, sodium chloride, copper sulfate, manganese chloride and zinc chloride, for example, are employed, either solely or in combination. The culture medium may be further added with, as appropriate, substances promoting the growth of the strain of S42227 or accelerating production of the sbustance, as well as commonly used defoaming agents such as silicon oil and Adecanol (Tradename). Any culture methods conventionally employed for the production of the substance may be employed for culturing the microorganism of the S42227 strain although the liquid phase culture methods, the deep stirring culture method in particular, are most suitable. The culture is carried out in aerobic conditions, and at a temperature of 24° to 29° C. The most desirable culturing temperature is in the neighborhood of 28° C. The production of the substance SS42227 reaches the maximum in 2 to 4 days after commencing the culturing, in either a shake or deep stirring culture.

The culture of the mycelia is terminated when the accumulated amount of the substance SS42227 in the culture broth reaches the maximum, and the aimed substances is separated from the both and purified. The separation and purification of the substances SS42227A and B may be performed by the application of various methods, either solely or appropriately combining two or more of them, taking into consideration the physicochemical properties of the substances as described hereinafter. More specifically, as the substance is usually contained in the culture broth, the cultured mycelia is first separated by centrifugation, filtration or the like means, and then from the culture fitrate substances SS42227A and B are separated and purified by using one or more of the conventional means such as, for example, solvent extraction, a method using inoexchange resins, gel filtration, absorption or partition column chromatography, dialysis, and precipitation.

One of the preferable methods of separating and purifying the substance SS42227A may be illustrated as follows: The culture broth is separated by centrifugation into broth supernatant and mycelia. The broth supernatant is extracted by a suitable solvent such as chloroform. The solvent is then distilled off from the extract, and the residue obtained is submitted to silica gel column chromatography. After the column has been eluted by a suitable eluent such as chloroform, for example, the active fractions are collected and concentrated in vacuo to obtain a residue, which is then dissolved in a suitable solvent such as n-hexane - ethyl acetate mixture to recrystallize and obtain substance SS42227A as colorless crystals.

An example of the preferable method for separating and purifying the substance SS42227B is as follows: The culture broth is separated by centrifugation into broth supernatant and mycelia. The broth supernatant is extracted by a suitable solvent such as chloroform. The solvent is then distilled off from the extract, and the residue is added with n-hexane and centrifuged. The precipitate thus obtained is washed with ether and subjected again to centrifugation. The thus-obtained precipitate is then dissolved in a small amount of chloroform, added with n-hexane, and centrifuged. The last procedure is again repeated to obtain substance SS42227B as colorless powder.

The substances SS42227A and B obtained as above have the following physicochemical and biological properties:

PHYSICOCHEMICAL PROPERTIES (1) Antibiotic SS42227A:
(a) Elementary analysis (as $C_{30}H_{33}N_3O_{10} \cdot CH_3COOC_2H_5$)

|  | C | H | N |
|---|---|---|---|
| Found (%) | 59.77 | 5.78 | 6.22 |
| Calculated (%) | 59.73 | 6.04 | 6.15 |

(b) Molecular formula
$C_{30}H_{33}N_3O_{10}$
(c) FAB - mass spectrum
$(M+H)^+ m/z$ 596
(d) Melting point
140° C. (decomposed)
(e) Ultraviolet absorption spectrum
See FIG. 1

| MeOH | 217 (52,000) |
|---|---|
| $\gamma$ nm($\epsilon$) | 248 (sh.) |
| max | 344 (5,000) |

Figure 2:
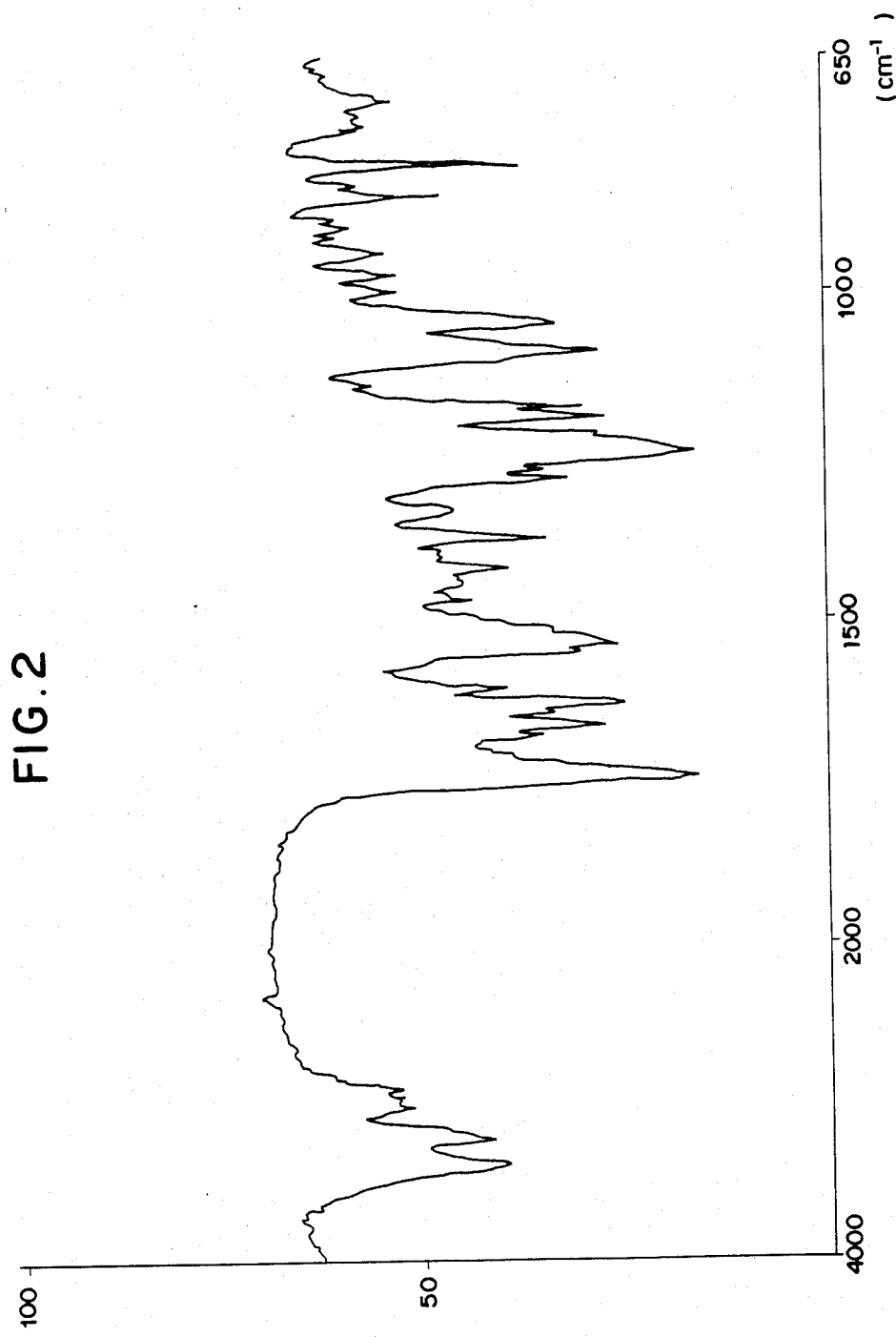
FIGS. 2 and 3 are the infrared spectrum and $^1$H-NMR spectrum of the same substance, respectively.
Figure 3:
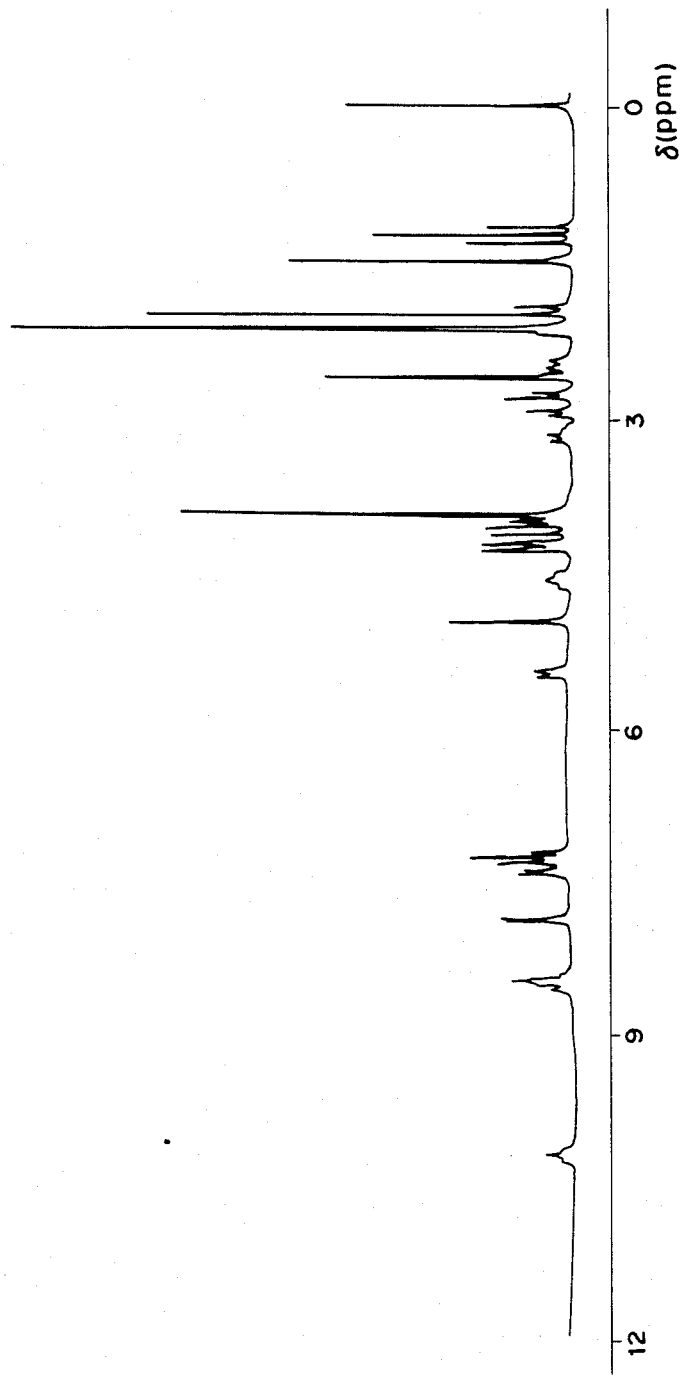

(f) Infrared absorption spectrum (KBr Method)
See FIG. 2
(g) $^1H$ - NMR spectrum (90 MHz)
See FIG. 3
Measured in a chloroform-d (CDCl$_3$) solution using TMS as a standard substance.
(h) $C^{13}C$ - NMR spectrum (22.5 MHz)
Measured in a chloroform-d solution using TMS as a standard substance.

$\delta$ (ppm): 202.6 (s), 172.7 (s), 165.7 (s), 163.8 (s), 163.2 (s), 156.0 (s), 149.6 (s), 134.4 (s), 133.1 (s), 128.4 (s), 127.7 (d), 126.9 (s), 125.1 (d), 123.9 (d), 121.8 (d), 120.1 (s), 108.6 (d), 84.0 (d), 76.9 (d), 76.7 (d), 56.0 (s), 55.6 (q), 53.7 (t), 50.6 (t), 45.4 (d), 35.8 (t), 27.2 (q), 20.7 (q), 20.0 (q), 17.0 (q)

(i) Solubility to solvents
Soluble to diethyl ether, choloroform, ethyl acetate, acetone and methanol. Sparingly soluble to n-hexane and water.
(j) Property as to basic, acid or neutral
Neutral
(k) Color and state of the substance
Colorless crystals (recrystallized from n-hexane/ethylacetate mixture)
(l) Coloring reaction
Positive to Dragendorff reagent.
(m) Thin layer chromatography
Carrier: Silica gel plate F$_{254}$ (product of Merck Inc.)

| Developing Solvent | $R_f$ |
|---|---|
| Chloroform-methanol 10:1 v/v | 0.65 |
| Chloroform-acetone 2:1 v/v | 0.34 |

(2) Antibiotic SS42227B:
(a) Elementary analysis ($C_{31}H_{33}N_3O_{11}$)

|  | C | H | N |
|---|---|---|---|
| Found (%) | 59.23 | 5.56 | 6.72 |
| Calculated (%) | 59.71 | 5.33 | 6.74 |

Figure 4:
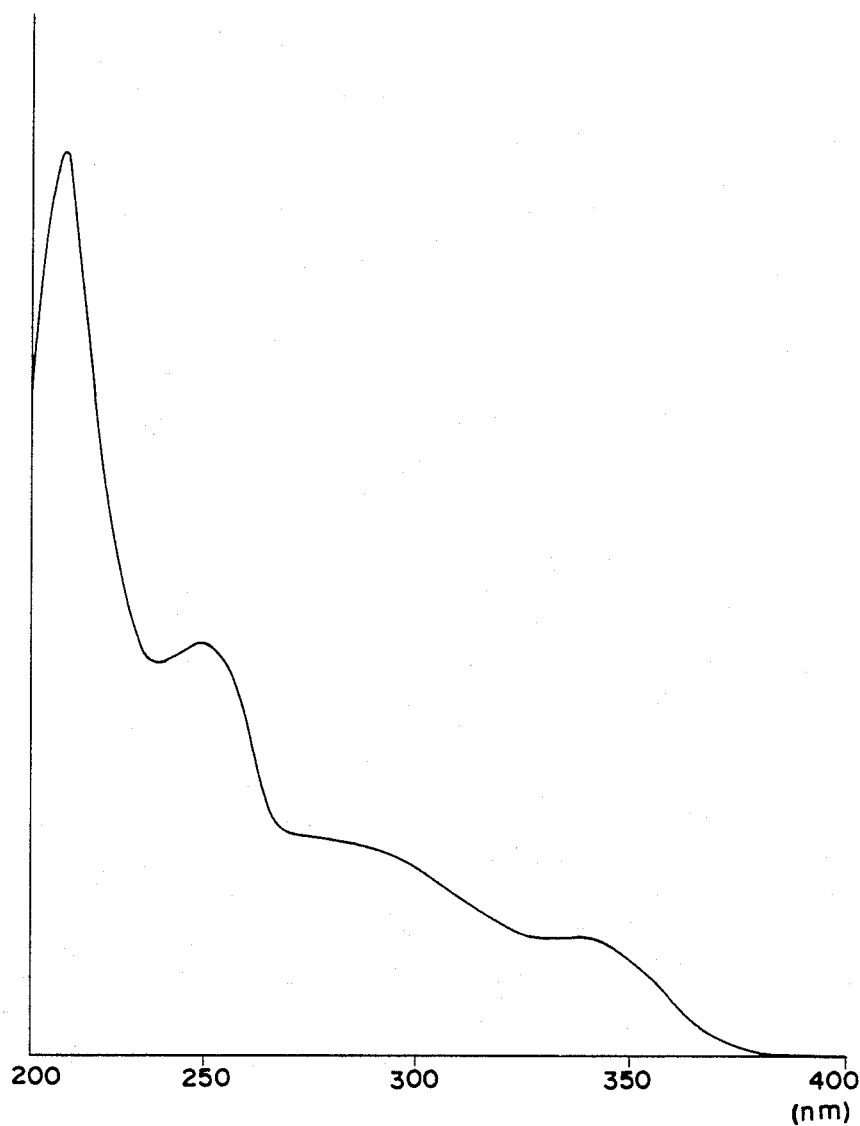
FIG. 4 shows the ultraviolet abosrption spectrum of the substance SS42227B of this invention.

(b) Molecular formula
$C_{31}H_{33}N_3O_{11}$
(c) FAB - mass spectrum
$(M+H)^+ m/z$ 624
(d) Melting point
190° C. (decomposed)
(e) Ultraviolet absorption spectrum
See FIG. 4

| MeOH | 217 (65,500) |
|---|---|
| $\gamma$ nm($\epsilon$) | 250 (30,400) |
| max | 290 (sh) |
|  | 340 (8,500) |

Figure 5:
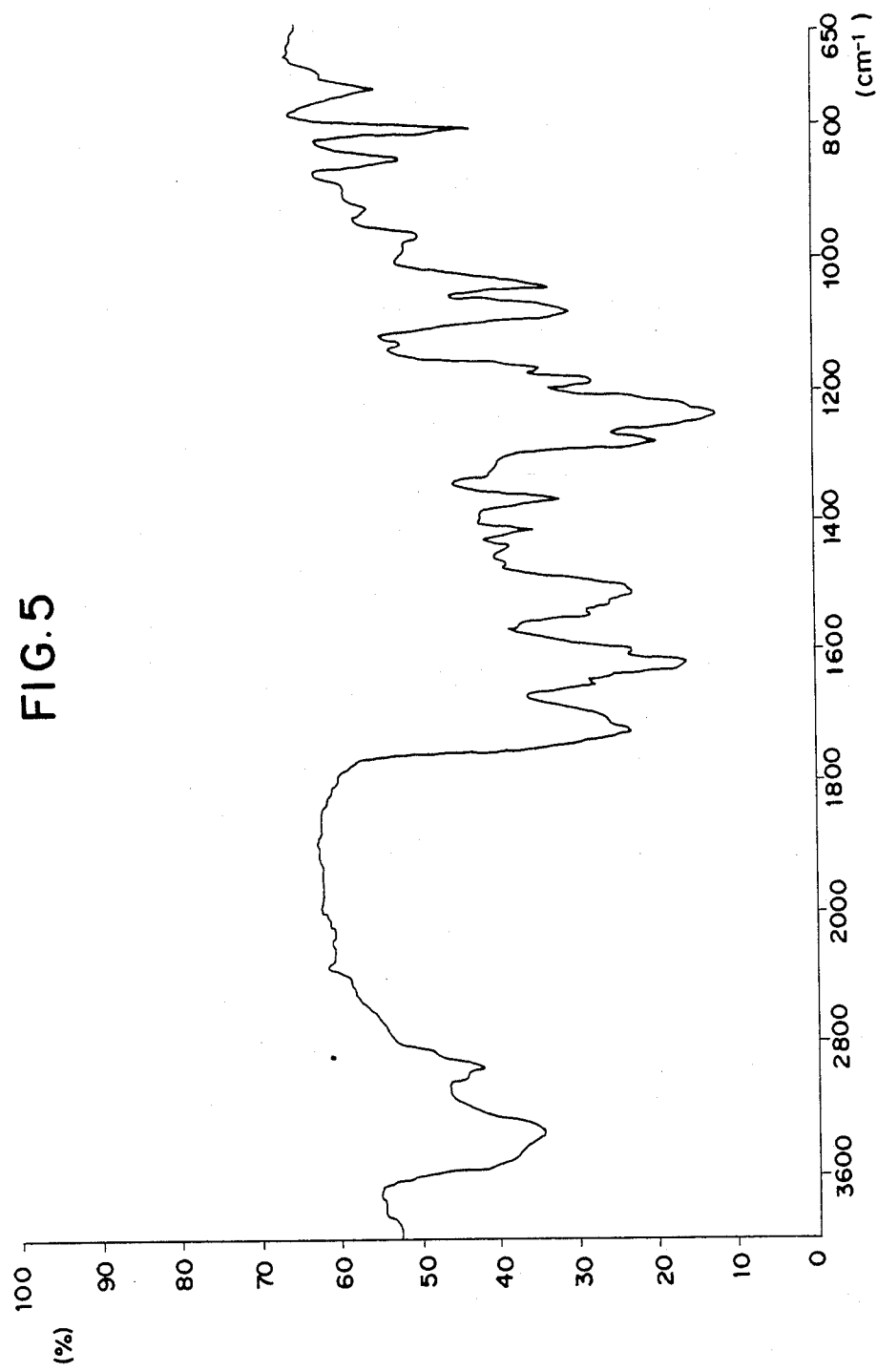
FIGS. 5 and 6 are the infrared spectrum and $^1$H-NMR spectrum of the same substance, respectively.
Figure 6:
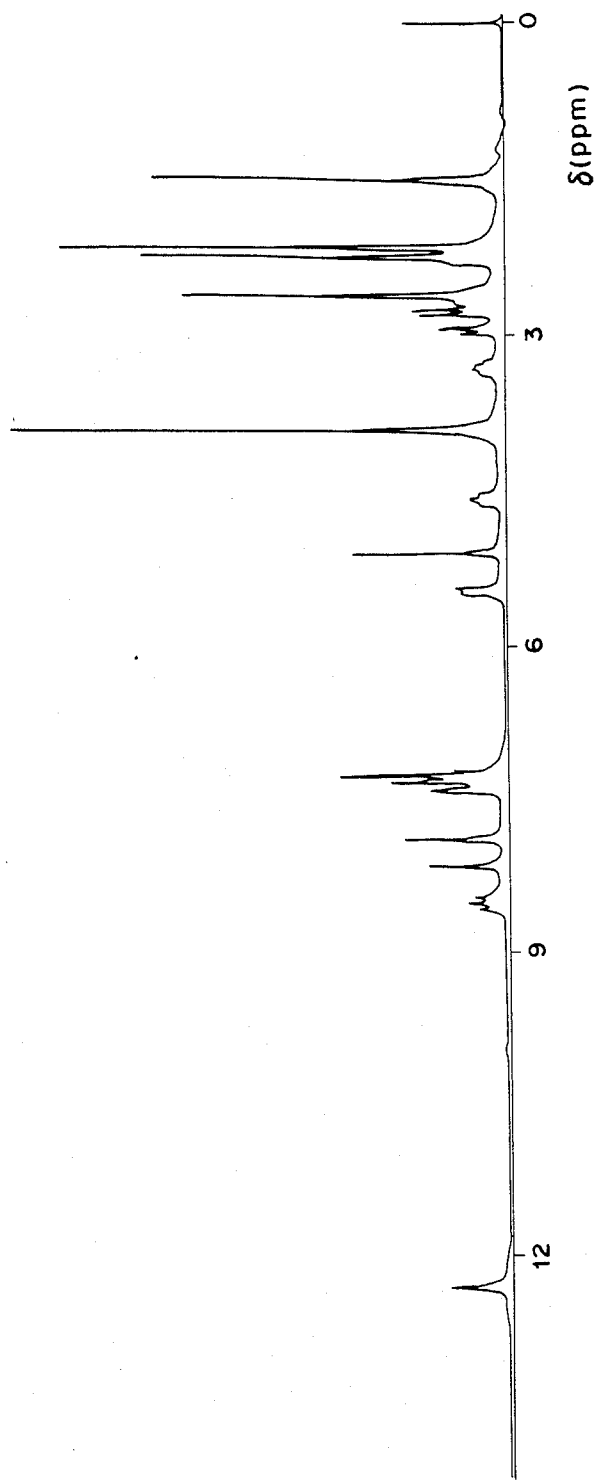

(f) Infrared absorption spectrum (KBr Method)
See FIG. 5
(g) $^1H$ - NMR spectrum (90 MHz)
See FIG. 6

Measured in a chloroform-d solution using TMS as a standard substance.

(h) $^{13}C$ - NMR spectrum (22.5 MHz)

Measured in a chloroform-d solution using TMS as a standard substance.

δ (ppm): 191.1 (s, br), 172.2 (s), 165.5 (s), 164.2 (s), 161.8 (s), 155.9 (s), 153.9 (s), 150.6 (d, br), 134.3 (s), 133.1 (s), 128.1 (s), 127.7 (s), 126.8 (s), 125.1 (d), 123.7 (d), 122.0 (d), 119.1 (s), 118.4 (s), 108.5 (d), 84.3 (d), 76.7 (d), 76.5 (d), 56.0 (s), 55.5 (q), 53.4 (t), 46.7 (d), 36.8 (t), 23.9 (q, br), 20.6 (q), 19.9 (q), 17.2 (q)

(i) Solublility to solvents

Soluble to chloroform, ethly acetate, acetone and methanol. Sparingly soluble to diethyl ether, n-hexane and water.

(j) Property as to basic, acid or neutral

Acid (k) Color and state of the substance

Colorless powder (l) Coloring reaction

Positive to Dragendorff reagent.

(m) Thin layer chromatography

Carrier: Silica gel plate $F_{254}$ (product of Merck Inc.)

| Developing Solvent | $R_f$ |
| --- | --- |
| Chloroform-methanol 10:1 v/v | 0.53 |
| Chloroform-acetone 2:1 v/v | 0.21 |

(n) $[a]_D^{25}$ +48°(C 0.48, $CHCl_3$)

BIOLOGICAL PROPERTIES

The substance SS42227 of this invention has the following biological properties.

(a) Antimicrobial Activity

Minimal inhibitory concentrations (MICs) of substances SS42227A and B against various microorganisms are shown in Table 1.

TABLE 1

| Microorganismus | Minimal Inhibitory Concentrations (MICs) (μg/ml) | |
| --- | --- | --- |
| | SS42227A | SS42227B |
| Bacillus subtilis ATCC 6633 | 0.78 | 50 |
| Staphylococcus aureus 209P | 6.25 | 50 |
| Staphylococcus aureus Terajima | 6.25 | 50 |
| Staphylococcus aureus Smith | 1.56 | 1.56 |
| Staphylococcus epidermidis ATCC 12228 | 6.25 | 100 |
| Sarcina lutea ATCC 9341 | <0.20 | <0.20 |
| Streptococcus faecalis IFO 12964 | 0.78 | 0.78 |
| Micrococcus lysodeikticus IFO 3333 | <0.20 | <0.20 |
| Escherichia coli 0-1 | >100 | >100 |
| Shigella flexneri 2b | <0.20 | 0.78 |
| Pseudomonas aeruqinosa IFO 13736 | >100 | >100 |
| Klebsiella pneumoniae ATCC 10031 | 3.12 | 50 |
| Proteus rettgeri | 100 | >100 |
| Serratia marcescens NHL | 100 | >100 |
| Candida albicans NHL 4019 | >100 | >100 |
| Aspergillus niger ATCC 9642 | >100 | >100 |
| Trichophyton tonsurans IFO 5928 | >100 | >100 |
| Pyricularia oryzae IAM 5016 | 100 | >100 |

(b) Antitumor Activities

Curing effects of substances SS42227A and B on mouse leukemia P-388 were examined according to the following method. The results are shown in Table 2. In the Table, the antitumor activities, or the effect of life prolongation, are expressed as the percentage of the survival time (days) of treated groups (T) per the survival time (days) for the untreated or control group (C).

TEST METHOD

CDF1 (male: supplied by Charles River Japan Inc.) were inoculated intraperitoneally with $1 \times 10^6$ P-388 cells. Then, commencing at 24 hours thereafter, substance SS42227A was intraperitoneally injected into the mice once a day and ten times in total.

TABLE 2

| Dose of SS42227A μg/kg/day | Antitumor Activity T/C (%) |
| --- | --- |
| 15.1 | 170 |
| 31.2 | 195 |
| 62.5 | 152 |
| 2 | 163 |
| 4 | 144 |
| 8 | 154 |
| 15 | 192 |
| 30 | 211 |
| 60 | 77 |

Judging from these antimicrobial and antitumor activities, the substance SS42227 of this invention is useful as an antimicrobial agent and a carcinostatic agent.

Other features of the invention will become apparent in the course of the following description of the exemplary enbodiments which are given for illustration of the invention and are not intended to be limiting thereof.

EXAMPLES

EXAMPLE 1

(i) A fluid culture medium containing 0.5% of a soluble starch and 0.5% of a cotton seed meal was adjusted to pH 7.0, 100 ml aliquot of which was poured into a 500 ml Sakaguichi flask and sterlized. The Streptomyces sp. S42227 (FERM p-8443) was inoculated to the medium and cultured by the shake culture method at 28° C. for two days to prepare the seed culture fluid.

Then, 16 liter of the fluid culture medium containing 0.5% of a soluble starch and 0.5% of a cotton seed meal and adjusted to pH 7.0, was charged to a 30 liter jar fermenter, to which 160 ml of the seed culture fluid prepared as above was inoculated and cultured at 28° C, under agitation 450 rpm, with aeration at a rate of 16 liter per minute, for 70 hours.

(ii) After completion of the culture, the culture broth was centrifuged and the broth supernatant was extracted with the same quantity of chloroform. The solvent was then distilled off in vacuo, and the crude extract obtained was submitted to silica gel (203 - 400 mesh, Kiesel Gel; Tradename, product of Merck Inc.) column chromatography (4.0 φ×40 cm) and eluted with chloroform/methanol (100/2) to obtain the active fraction.

(iii) The aimed substance thus obtained was concentrated to dryness and recrystallized from n-hexane-ethyl acetate mixture to obtain 20 mg of colorless crystals of SS42227A.

The physicochemical properties of this substance were as described above.

EXAMPLE 2

(i) A cultured material prepared in the same manner as in Example 1 (i) was centrifuged and the broth supernatant was extracted with the same amount of chloroform. The crude extract obtained by distilling off the solvent in vacuo was added with n-hexane and centrifuged at 3,000 rpm to obtain a brownish powder. The powed was washed with ether, sissolved in a small amount of chloroform, added with n-hexane and centrifuged at 3,000 rpm to obtain a pale yellowish poweder. The pale yollowish powder was dissolved in 50 ml of chloroform, added with a small amount of n-hexane, an centrifuged at 3,000 rpm to remove the precipitate. The remaining mother liquor was added with 100 ml of n-hexane, and centrifuged at 3,000 rpm to obtain 130 mg of a colorless powed of SS42227.

The substance thus prepared has the same physicochemical properties as described above.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by letters patent of the United States is:

1. substance represented by the following formula (I):

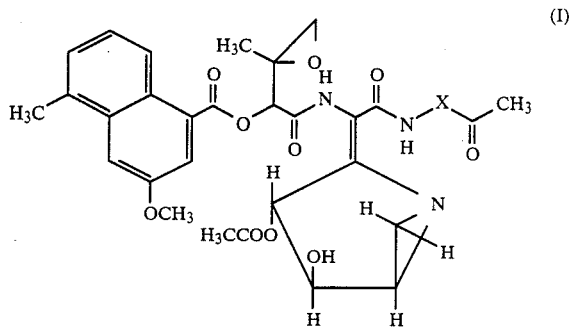

in which X represent $>CH_2$ or $>C=CHOH$.

2. A substance as claimed in 1 wherein X in the formule (I) is $>C_2$.

3. A substance as claimed in 1 wherein X in the formula (I) is $>CH=CHOH$.

* * * * *

UNITED STATES PATENT AND TRADEMARK OFFICE
CERTIFICATE OF CORRECTION

PATENT NO. : 4,835,287

DATED : May 30, 1989

INVENTOR(S) : NAGAOKA ET AL

It is certified that error appears in the above-identified patent and that said Letters Patent is hereby corrected as shown below:

Column 8, lines 10-22, Table 2 should be cancelled, and replaced with Tables 2-A and 2-B below:

Table 2-A

| Dose of SS42227A $\mu$g/kg/day | Antitumor Activity T/C (%) |
|---|---|
| 15.1 | 170 |
| 31.2 | 195 |
| 62.5 | 152 |

UNITED STATES PATENT AND TRADEMARK OFFICE
CERTIFICATE OF CORRECTION

PATENT NO. : 4,835,287
DATED : May 30, 1989
INVENTOR(S) : NAGAOKA ET AL

Page 2 of 2

It is certified that error appears in the above-identified patent and that said Letters Patent is hereby corrected as shown below:

Table 2-B

| Dose of SS42227B $\mu$g/kg/day | Antitumor Activity T/C (%) |
|---|---|
| 2 | 163 |
| 4 | 144 |
| 8 | 154 |
| 15 | 192 |
| 30 | 211 |
| 60 | 77 |

Column 10, line 20, "$C_2$" should read --$CH_2$--.

Signed and Sealed this

Tenth Day of April, 1990

Attest:

HARRY F. MANBECK, JR.

*Attesting Officer*  *Commissioner of Patents and Trademarks*